United States Patent
Blum et al.

(10) Patent No.: US 10,449,509 B2
(45) Date of Patent: Oct. 22, 2019

(54) SYNTHESIS OF ORGANIC PEROXYDES USING AN OSCILLATORY FLOW MIXING REACTOR

(71) Applicant: Arkema France, Colombes (FR)

(72) Inventors: Albert Blum, Weissenhorn (DE); Philippe Maj, Berignais (FR); Serge Hub, Villeurbanne (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/768,684

(22) PCT Filed: Oct. 26, 2016

(86) PCT No.: PCT/EP2016/075834
§ 371 (c)(1),
(2) Date: Apr. 16, 2018

(87) PCT Pub. No.: WO2017/072190
PCT Pub. Date: May 4, 2017

(65) Prior Publication Data
US 2018/0304227 A1    Oct. 25, 2018

(30) Foreign Application Priority Data
Oct. 26, 2015    (FR) .................................... 15 60186

(51) Int. Cl.
*C07C 407/00* (2006.01)
*B01J 19/24* (2006.01)
*B01J 19/00* (2006.01)

(52) U.S. Cl.
CPC ......... *B01J 19/241* (2013.01); *B01J 19/0006* (2013.01); *B01J 19/248* (2013.01); *C07C 407/00* (2013.01); *B01J 2219/00033* (2013.01); *B01J 2219/00159* (2013.01); *B01J 2219/00164* (2013.01)

(58) Field of Classification Search
CPC .. C07C 407/00; C07C 409/38; B01J 19/0006; B01J 19/241; B01J 19/248; B01J 2219/00033; B01J 2219/00159; B01J 2219/00164
See application file for complete search history.

(56) References Cited

U.S. PATENT DOCUMENTS

| | | | |
|---|---|---|---|
| 3,167,395 A * | 1/1965 | Marshall | B01J 19/185 422/131 |
| 4,444,961 A | 4/1984 | Timm | |
| 2015/0336886 A1* | 11/2015 | Lampe | C07C 409/38 560/302 |

FOREIGN PATENT DOCUMENTS

| WO | WO-2012/095176 | | 7/2012 |
|---|---|---|---|
| WO | WO2012095176 | * | 7/2012 |
| WO | WO-2014/044624 | | 3/2014 |
| WO | WO2014044624 | * | 3/2014 |

OTHER PUBLICATIONS

WO2014044624 translated 5 pages (Year: 2014).*
International Search Report dated Jan. 18, 2017 for PCT/EP2016/075834.

* cited by examiner

*Primary Examiner* — Jafar F Parsa
*Assistant Examiner* — Blaine G Doletski
(74) *Attorney, Agent, or Firm* — NK Patent Law

(57) ABSTRACT

The present invention concerns a method and an apparatus (10, 20) for a continuous preparation of organic peroxides, with the reactor comprising at least one flow channel (1, 1*a*, 1*b*) configured as a reaction zone; an inlet system (2) in fluid communication with a first end of the at least one flow channel and configured for introducing two or more substances or a combination of substances into the at least one flow channel; an outlet system (3) in fluid communication with a second end of the at least one flow channel, the second end being located downstream of the first end and the outlet system being configured for extracting a reaction product present at the second end; an oscillatory system (4, 5) configured for superimposing an oscillatory flow on the flow of substances passing through the at least one flow channel, the oscillatory being effected in at least a section of the at least one flow channel; and a controller configured to implement the method by controlling the inlet system to introduce, according to a first time characteristic, at least two substances or a combination of substances into the at least one flow channel, the oscillatory system to superimpose an oscillatory flow on at least a part of the flow of substances passing through the at least one flow channel, and the outlet system to extract, on an ongoing basis, the reaction product formed in the flow channel from the substances introduced such that the output mass flow rate corresponding to the sum of the input mass flow rates.

13 Claims, 4 Drawing Sheets

SYNTHESIS OF ORGANIC PEROXYDES USING AN OSCILLATORY FLOW MIXING REACTOR

CROSS-REFERENCE TO RELATED APPLICATIONS

Figure 1:
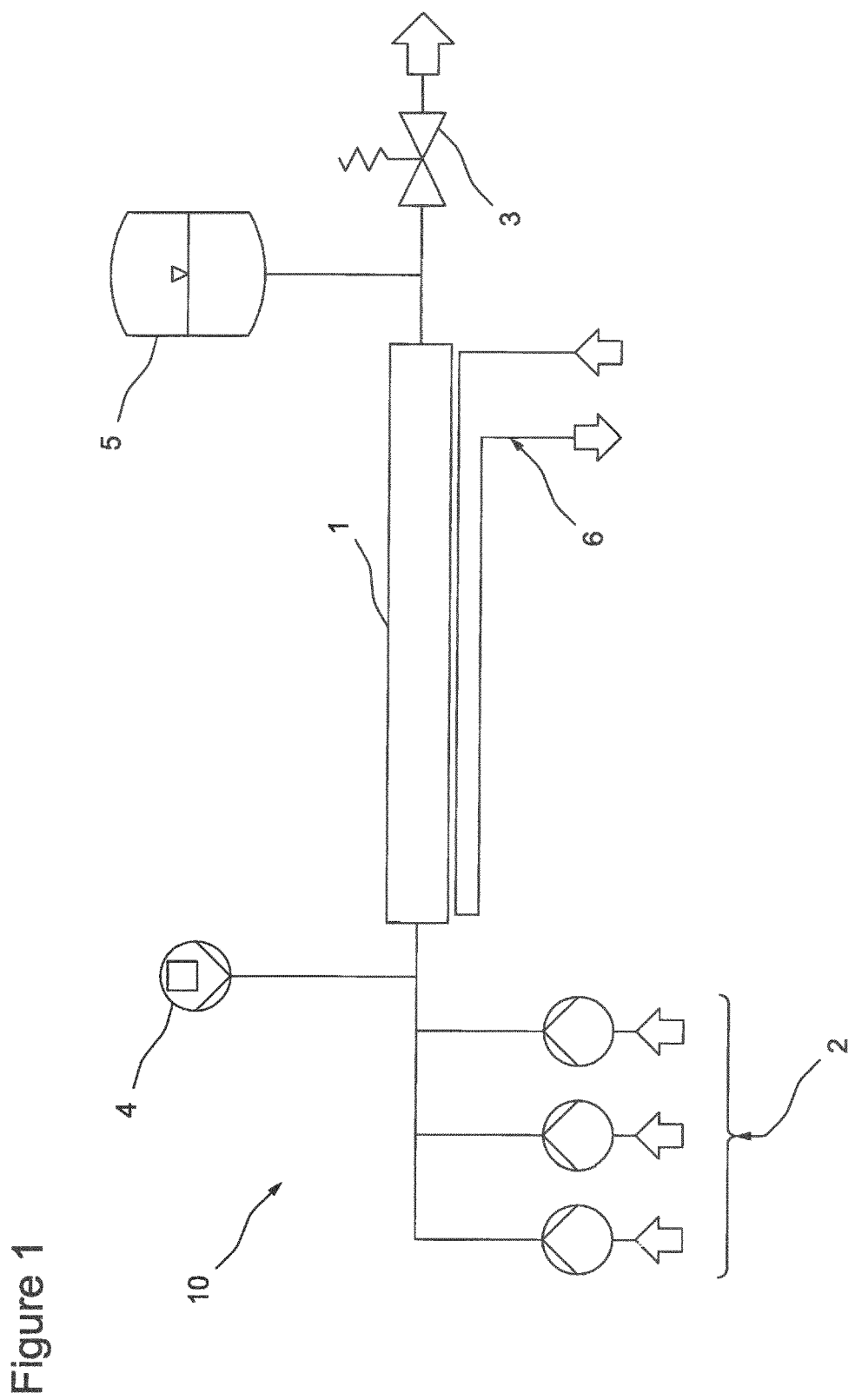

This application is a U.S. National Stage application of International Application No. PCT/EP2016/075834, filed Oct. 26, 2016, which claims the benefit of French Application No. 1560186, filed Oct. 26, 2015.

FIELD OF THE INVENTION

The present invention relates to an efficient and safe synthesis of organic peroxides, and in particular to a continuous synthesis of organic peroxides under oscillating flow conditions.

BACKGROUND OF THE INVENTION

Organic peroxides play an important role as initiators in the preparation of polymers or as oxidizers in medical preparations and complex chemical syntheses.

Organic peroxides are thermally sensitive, highly reactive compounds known to decompose in a self accelerating exothermic reaction when not kept at a low enough temperature. Onset and progress of a respective self accelerating reaction, depend not only on the temperature, but also on the heat dissipation conditions at which a respective organic peroxide is kept. A SADT (Self Accelerating Decomposition Temperature) defining the lowest temperature at which the exothermic decomposition may start, thus does not represent an absolute value but reflects also the conditions under which the respective organic peroxide is kept. Smaller packages usually have a higher surface/volume ratio than bigger packages, and therefore better heat dissipation conditions which result in higher SADTs.

Due to their thermal instability, a synthesis of organic peroxides requires a very precise temperature control to avoid any serious incidents. Since the respective production or preparation processes use a bi-phase or multiphase reaction of immiscible phases, a thorough mixing of the reaction components is required to achieve a satisfactory reaction rate.

Organic peroxides may be produced in discontinuous or continuous processes. In discontinuous processes, the reactants are either all loaded into a reactor (batch reaction) or one reactant or catalyst is dosed to the other reactants provided in a reactor (semi batch reaction). The ratio between the reaction volume and the cooling surface available in such reactors is usually high, making a precise temperature control difficult and thus limiting the amount of organic peroxides to be produced safely within one lot.

For larger production volumes, continuous preparation processes are therefore preferred, where the supply of the starting materials and the extraction of the final product occurs on a continuous basis.

L. Fritzsche and A. Knorr describe in "Transformation of the $2^{nd}$ step of a peroxyester synthesis from semi-batch to continuous mode", Chemical Engineering and Processing 70 (2013) 217-221, a transformation of organic peroxide synthesis from semi-batch to continuous mode. The reaction is performed in a tubular continuous flow reactor exposed to ultrasound for improved mixing and increase of interface of phase boundary and thus better mass transfer between the two phases.

In "Continuous synthesis of a high energetic substance using small scale reactors", Chemical Engineering Transactions, 32 (2013) 685-690, L. Fritzsche and A. Knorr describe a "split-and-recombine" (SAR) reactor where two meandering channels repeatedly split and recombine along the whole of their lengths. The SAR reactor is used for TBPEH (tert-Butyl peroxy-2-ethylhexanoate) synthesis with application of ultrasound.

Document WO 2008/006666 A1 e.g. describes a continuous process for the preparation of acyl peroxides using a reactor with two reaction zones. The first reaction zone is configured as a loop reactor where most of the bi-phase reaction mixture is circulated in a cooled loop, while part of it, or more precisely between 20% and 50% of the circulating volume, is sup-plied to the second reaction zone and replaced by a corresponding amount of newly fed starting materials. The second reaction zone is formed by a stirred cell reactor where two or more reaction cells are connected in series with the content of each of the reaction cells being mixed by at least one stirrer. The reaction cells are connected to one another such that there is virtually no backmixing of the reaction mixture from a downstream reaction cell into an upstream reaction cell. Though enabling a continuous preparation of organic peroxides, the processing in the second reaction zone represents a sequence of CSTRs (continuous stirred tank reactors) rather than a continuous flow-through reactor, since the second reaction zone is organized in a cascade of cells with each cell processing a certain part of the total reaction volume for a specified period. Due to the cell processing, the ratio between the cooling surface and the volume of the reaction mixture is in the second reaction zone still comparatively poor, thus limiting the throughput of the reactor or requiring a large number of reaction cells. Different to a continuous flow reaction, the stirring results in a remixing of portions where the conversion is in an advanced state with portions where the conversion is still poor. Due to this, CSTRs require numerous cells to get a good final conversion. As a further consequence of the remixing, the mechanical stirrers provide no finely dispersed mixing of the phases resulting in a comparatively low conversion and/or long residence time (time required for the reaction mixture to pass through the reactor).

Flow-through reactors such as, for instance, tube reactors, plate reactors or the like enable a continuous preparation of organic peroxides in a continuous flow. Flow-through reactors comprise at least one reactor channel for the reaction mixture to pass through, whereby when more than one reactor channel is used, the channels can be connected in parallel and/or in series. Due to the reaction mixture flowing continuously through the reactor channels, a local concentration of the reaction components is basically a function of the distance traversed by the reaction mixture along the length of the reactor channel(s) to the respective position, and can be described by way of the plug flow reactor model. In other words, the concentration of the reaction mixture components is assumed to change only along its flow direction while having no gradients transverse to the flow direction.

Phase mixing in flow-through reactors is usually accomplished by creating turbulences, i.e. irregular local flows with directions different to the main flow direction. Turbulences can either be created by means of high flow rates (usually characterized by a Reynolds number above 3,000 or so) or by introducing redirection means into the flow path like baffles (see e.g. WO 1999/55457 A1), or by channel wall irregularities (e.g. helical protrusions or indentations as disclosed in WO 2006/092360 A1), or by changes in the reaction channel or flow path direction (as for instance described in WO 2012/095176 A1) or by splitting and recombining the flow (e.g. herring bone structures as described in WO 2014/044624 A1). Turbulences not only provide a thorough mixing of the immiscible phases present in the synthesis of organic peroxides, but usually also result in smaller maximal droplet sizes than are possible with mechanical agitation means like stirrers or the like. Smaller maximal droplet sizes in turn provide larger reaction surfaces causing higher reaction rates and thus shorter reaction times. Since a mixing based on turbulences requires no moving parts, respective reactors are also referred to as static mixers.

Process conditions for synthesizing organic peroxides can be improved by using so-called mini-reactors. Mini-reactors are characterized by having flow channel dimensions (transverse to the main flow direction) in the millimeter (milli-reactors) or even in the micrometer (micro-reactors) range. A use of mini-reactors reduces the local reaction volume significantly, while increasing at the same time the ratio between the reactor channel surface available for cooling and the reactor channel volume. This enables an improved control of local reaction temperatures that, together with the smaller local volumes, improves the safety of the preparation process.

One example for a continuous flow-through mini reactor is a plate exchanger as e.g. described in document WO 2007/125091 A1. The plate exchanger comprises three plates arranged to form reactor channels and heat exchange channels between them. The reactor can be used for synthesizing organic peroxides for which two reactor channels are connected in series. Two reactants are fed to a first of the two reactor channels to form an intermediary product which is then fed to the other of the two reactor channels together with a third reactant to form the final product. A heat transfer fluid runs through the heat exchange channels for dissipating the reaction heat.

Another example for a continuous flow-through mini reactor is disclosed in WO 2014/044624 A1. The reactor comprises at least two comb-like structures with angled teeth. One of the two structures is disposed on top of the other such that the teeth of the two structures cross over. The thus combined structures are placed into a housing covering its top and bottom faces to form crossing pathways along which a fluid is forced to change its flow direction repeatedly. For enabling a preparation of organic peroxides, the housing is placed in a tube passed through by a cooling liquid.

The flow-through mini reactor disclosed in WO 2012/095176 A1 provides a reaction channel, which pathway directions change repeatedly. The reaction channel is formed in a plate cov-ered by a further plate. To intensify the turbulences and thus improve the mixing of the processed fluid, an oscillatory flow is superimposed on the fluids steady flow.

The oscillatory flow is limited to a region between the inlet for the starting materials and the outlet for the final product and results in recurring high flow rates inside the reactor. The term "oscillatory flow" signifies a variation of the flow rate with time, whereby the average flow rate of an oscillatory flow equals zero. When superimposing an oscillatory flow on a steady flow, the average flow rate is thus given by the rate of the steady flow. Due to the temporary higher flow rates, however, stronger turbulences are created that result in a more efficient mixing of the reaction mixture components. The residence time of the reaction mixture is not affected by the oscillatory flow, since the average flow rate still equals the steady flow rate.

A superimposition of an oscillatory flow on a steady flow has already been described in patent specification U.S. Pat. No. 4,271,007 as a proper means for preventing a deposition of solids on the walls of a tubular reactor used for high-temperature hydrocarbon cracking. The oscillation frequency used was 115 Hz. WO 2012/095176 A1 describes a use of an oscillatory flow in a mini-reactor which reactor channel is configured with repeated pathway changes. The oscillatory flow is superimposed on a steady flow to effectively mix a suspension being processed such that a deposition of solid material in the reactor is prevented and no sedimentation, fouling or clogging of the reactor has to be worried about.

A preparation of organic peroxides in continuous flow reactors is at present effected under steady flow conditions where the local flow rates do not change with time. To achieve a required mixing of the components in the reaction mixture, the flow rate of the reaction mixture has to be high enough to cause turbulent flow conditions. In this context it is noted that although turbulences introduce chaotic flow conditions, the flow rate through a section of the reactor (a length of the flow channel) does not generally change with time, and the term steady flow conditions is in this document therefore also used for turbulent flows, where the pattern of the fluid's movement along the length of the reactor's pathway does not change with time. The term "steady flow" as used in this specification refers not only to a (possibly slowly and/or slightly changing) constant flow but also to more or less periodic intermittent flow characteristics like pulsating flows, which intermission periods are much shorter than the reaction time, e.g. by a factor of ten or more.

Since a synthesis of organic peroxides has to be carried out at relatively low temperatures, the reaction times required are comparatively long. In order to complete a respective synthesis to the desired extent in a flow-through reactor operated under steady flow conditions, the reaction mixture has to reside in the reactor for the whole of the reaction time required. The length of time that elapses between an introduction of starting materials and the output of a final product synthesized from these starting materials is called residence time and corresponds to the above reaction time. Together with the flow rate of the reaction mixture, this time period defines the length of the reaction pathway required. The higher the necessary flow rate and the longer the residence time, the longer the flow channel defining the pathway.

A synthesis of organic peroxides also requires an efficient temperature control of the reaction medium. The lateral dimensions of the flow channel, i.e. its dimensions transverse to the flow direction defined by it, have therefore to be, at least in one direction, small enough to guar-antee an effective heat transfer. Due to this cross sectional limitations, a long flow channel accordingly implies a high flow resistance. High flow resistances in turn result in considerable pressure drops that are difficult to handle and can make an implementation of a respective reactor a technical challenge. In addition, long reaction flow channels also imply large reaction volumes which in the case of peroxides give rise to serious risks.

There is therefore a desire for a process and an apparatus enabling a safe large-scale synthesis of organic peroxides under continuous flow-through conditions.

SUMMARY OF THE INVENTION

The above is achieved by the invention as defined in the independent claims.

A respective process for a continuous preparation of organic peroxides comprises the step of providing a continuous flow reactor having at least one flow channel configured as a reaction zone; an inlet system being in fluid communication with a first end of the at least one flow channel and being configured to introduce two or more substances or a combination of substances into the at least one flow channel; an outlet system in fluid communication with a second end of the at least one flow channel, the second end being located downstream of the first end and the outlet system being configured to extract a reaction product present at the second end; and an oscillatory system configured for superimposing an oscillatory flow on the flow of substances passing through the at least one flow channel, the oscillatory flow being effected in at least a section of the at least one flow channel. The process for a continuous preparation of organic peroxides further comprises the steps of introducing, according to a first time characteristic, at least two substances or a combination of substances into the at least one flow channel; superimposing by use of the oscillatory system an oscillatory flow on at least a part of the flow of substances passing through the at least one flow channel to create turbulences in the flow of substances; and extracting the reaction product formed in the at least one flow channel from the substances introduced, whereby the extraction is performed on an ongoing basis using the outlet system, with the output mass flow rate corresponding to the sum of the input mass flow rates.

In this context it is noted that the terms "including", "comprising", "containing", "having", and "with", as well as grammatical modifications thereof used in this specification and the claims for listing features, are generally to be considered to specify a non-exhaustive listing of features, such as, for instance, method steps, components, ranges, dimensions or the like, and do by no means preclude the presence or addition of one or more other features or groups of other or additional features. Further it is noted that the term "reaction product" as used in this document specifies the result of a reaction having taken place in the reaction zone(s) of the reactor and not only the product of a chemical reaction based on the starting materials. It is also appreciated that the term "substance" is used to specify a starting material in the meaning of a reactant or reagent as well as in the meaning of a mixture of reactants with one or more other materials like e.g. a solvent or a catalyst or the like, and that the term "flow of substances" includes not only the substances introduced but also possible reaction products already brought about in the process. The term "substances" in particular specifies those reactants, additives and solvents, necessary and used for the preparation of an organic peroxide. Finally it is pointed out that the term "ongoing" is used in this specification to characterize any process or operation performed continuously or intermittently and not in separate portions like as characteristic for a batch-wise processing.

Advantageously, the step of providing a continuous flow reactor comprises providing a reactor further having a temperature control system adapted to control the temperature profile along the length of the at least one flow channel, and wherein the method further comprises the step of controlling the temperature profile along the at least one flow channel using the temperature control system.

Also, the step for superimposing an oscillatory flow on at least a part of the flow of substances passing through the at least one flow channel comprises a use of an oscillatory system having an oscillatory flow generating device being in fluid communication with the at least one flow channel at a first position and a hydraulic accumulator being in fluid communication with the at least one flow channel at a second position different from the first position.

The process is advantageously performed in an apparatus configured as continuous flow reactor that comprises at least one flow channel configured as a reaction zone; an inlet system in fluid communication with a first end of the at least one flow channel and configured for introducing two or more substances or a combination of substances into the at least one flow channel; an outlet system in fluid communication with a second end of the at least one flow channel, the second end being located downstream of the first end and the outlet system being configured for extracting a reaction product present at the second end; an oscillatory system configured for superimposing an oscillatory flow on the flow of substances passing through the at least one flow channel, the oscillatory flow being effected in at least a section of the at least one flow channel; and a controller configured to control the inlet system to introduce, according to a first time characteristic, at least two substances or a combination of substances into the at least one flow channel, the oscillatory system to superimpose an oscillatory flow on at least a part of the flow of substances passing through the at least one flow channel, and the outlet system to extract, on an ongoing basis, the reaction product formed in the flow channel from the substances introduced such that the output mass flow rate corresponding to the sum of the input mass flow rates.

With a preparation process and an apparatus as specified above, the turbulent flow conditions required for a thorough mixing of the reaction components can be achieved to a large extent independent of the delivery rate of the continuous flow reactor. While the delivery rate is basically defined by the reactor's average flow capacity and hence the mass flow introduced via the inlet system, the turbulent flow conditions are defined by the effective flow rates which are, due to the superimposed oscillatory flow, repeatedly higher than the average flow rate. By achieving turbulent flow conditions without being required to increase the average flow rate of the reaction mixture, shorter flow-through reactors can be used and the volume of the material being in process can thus be reduced. Since the oscillatory flow supports a reduction in the maximal droplet size and an increase of the minimal droplet size of bi-phase mixtures, it may also be used to advance the reaction, to reduce the residence time required, to reduce side reactions, and avoid formation of emulsions difficult to separate. While the residence time may be controlled now only by adjusting the flow of the substances introduced via the inlet system, the reaction kinetics may independently be controlled by the oscillating flow conditions.

With the oscillatory flow rates being adjustable independent of the average flow rate, flow-through reactors can be used that are free of small jets, baffles, orifices or other obstacles increasing reactor's cost, impairing its flow resistance, giving rise to material depositions and clogging, and also resulting in an irregular distribution of droplet sizes raising the risk for a presence of very low reaction "dead" zones and very fast reaction "hot" spots. The application of an oscillatory flow to respective flow-through reactors results in a uniform distribution of droplets, the size of which is defined by the oscillatory flow conditions and determines the mass transfer taking place in the reaction, thereby enabling an easy to control preparation process with very good space-time-yields (amount of product obtained per unit reactor volume and unit of time).

Since the ratio of the surface surrounding the reaction mixture relative to the volume sur-rounded by the surface is in flow-through reactors high enough to enable an effective removal of heat generated in the course of the chemical transformation process, reaction temperatures above the SADT defined for the respective organic peroxide when stored in a container can be used without running a risk which results in shorter reaction times.

Being able to adjust reaction kinetics and residence times independent from each other to different reactor architectures, there are no restrictions with regard to a type of flow-through reactor to be used, a type of organic peroxides to be produced, or the reaction kinetics (fast or slow) to be applied. By being able to adapt an organic peroxide production process to a given flow-through reactor architecture and to optimize the preparation process with respect to a maximum space-time-yield possible without being required to modify the reactor itself or to run the reaction process outside safety constraints, set-up times as well as downtimes for different production runs can thus be minimized.

Preferred embodiments of the preparation method further comprise the step of providing a continuous flow reactor that provides a temperature control system adapted to control the temperature profile along the length of the flow channel, and a further method step of controlling the temperature profile along the at least one flow channel using the temperature control system. The further method step is advantageously performed by the reactor's controller which is for this purpose further configured for controlling the temperature control system to control the temperature profile along the at least one flow channel.

Some configurations of the above defined temperature control system may further allow for a control of the temperature profile in sections such that a temperature profile in one section of the at least one flow channel may be controlled independent of a temperature profile in another section of the at least one flow channel. Respective temperature control systems and controls enable a precise setting of reaction temperatures which may also be set to vary along the length of the at least one flow channel if need be.

According to advantageous embodiments, an introduction of the at least two substances according to the first time characteristic comprises an introduction of at least one of the two substances in a constant or in a pulsating manner. Introducing the one or more substances in a pulsating manner does not affect the reaction process in the reactor and allows a use of pulsating pumps like (multihead) membrane or piston dosing pumps without need for a snub-ber.

Preferred embodiments may have the step for superimposing an oscillatory flow on at least a part of the flow of substances passing through the at least one flow channel be performed by using an oscillatory system comprising an oscillatory flow generating device being in fluid communication with the at least one flow channel at a first position and a hydraulic accumulator being in fluid communication with the at least one flow channel at a second position different from the first position. Using a respective oscillatory system enables a back and forth shifting of a reaction mixture volume between the oscillatory flow generating device and the hydraulic accumulator and through at least a part of the least one flow channel without affecting the operation of the inlet and the outlet system.

Preferred embodiments may further have the step of providing a continuous flow reactor which at least one flow channel comprises a first flow channel and a second flow channel, a first end of the first flow channel being in fluid communication with the inlet system and a second end of the first flow channel being in fluid communication with a first end of the second flow channel. A respective reactor further comprises a recirculation system configured for reintroducing a portion of the reaction mixture output from the second end of the first flow channel into the first flow channel upstream of its second end. Respective preferred embodiments of the preparation method further comprise the step for reintroducing a portion of the reaction mixture output from the second end of the first flow channel into the first flow channel upstream of its second end using the recirculation system.

Advantageously, the step of providing a continuous flow reactor comprises providing the first flow channel formed by three flow channel modules connected in series, whereby the first flow channel module and the second flow channel module are each formed by split-and-recombine reactor, while the third flow channel module is formed by a meandering channel reactor, and wherein the inlet system is configured to introduce a first substance to a first inlet of the first flow channel module and to introduce a second substance to a first inlet of the second flow channel module, with the outlet of the first flow channel module being in fluid communication with a second inlet of the second flow channel module, the outlet of the second flow channel module being in fluid communication with the inlet of the third flow channel module, and the outlet of the third flow channel module being in fluid communication with a recirculation system configured for reintroducing a portion of the reaction mixture output from the third flow channel module into a second inlet of the first flow channel module.

Advantageously, the recirculation system comprises the oscillatory flow generating device and wherein the hydraulic accumulator is in fluid communication with the second end of the second flow channel.

The step is preferably carried out by the controller, which is for this purpose further adapted to control the recirculation system to reintroduce a portion of the reaction mixture output from the second end of the first flow channel into the first flow channel upstream of its second end.

Configurations of respective embodiments have the recirculation system advantageously comprise an oscillatory flow generating device whereby a hydraulic accumulator is in fluid communication with the second end of the second flow channel. In such embodiments, the oscillatory flow generating device effects both, a reintroduction of a portion of the reaction mixture output from the second end of the first flow channel, and a superposition of an oscillatory flow on a steady flow in the second flow channel.

In some configurations of such embodiments, the step of controlling the temperature profile along the at least one flow channel using the temperature control system further comprises a use of a temperature control system having a first heat exchange system and a second heat exchange system, the first heat exchange system adapted for a heat exchange with the first flow channel and the second heat exchange system adapted for a heat exchange with the second flow channel, thereby enabling a control of the temperature profile along the first flow channel separate from the temperature profile along the second flow channel. The step is preferably accomplished by the controller, which is for this purpose further adapted to con-trot the temperature profile along the first flow channel separate from the temperature profile along the second flow channel. Respective configurations allow for an optimized adaptation of the temperature profiles to the different reaction conditions present in the two flow channels.

In advantageous embodiments of an above preparation method, the step of providing a continuous flow reactor comprises a provision of a reactor that further comprises an additional inlet system configured for introducing one or more substances into the at least one flow channel downstream of its first end, and wherein the method further comprises the step of introducing one or more additional substances into the at least one flow channel downstream of its first end according to a second time characteristic, and the output mass flow rate effected by the outlet system further also includes the additional input mass rate. The step is preferably carried out by the controller, which is for this purpose further configured to control the additional inlet system for introducing one or more additional substances into the at least one flow channel downstream of its first end according to a second time characteristic, and to control the outlet system to effect the output mass flow rate further also including the additional input mass rate. A respective additional inlet system enables a more precise control of the reaction processes desired and enhances the versatility of the preparation process.

According to preferred embodiments, the step of providing a continuous flow reactor comprises a provision of a reactor which oscillatory system is configured to generate an oscillatory flow having a frequency of between 0.1 Hz and 500 Hz, more preferably of between 1 to 50 Hz, and even more preferably of between 2 Hz to 25 Hz. Respective oscillation fre-quencies ensure an actual oscillatory movement of the reaction mixture which forms the basic requirement for a creation of the turbulences necessary for the mixing of the mixture.

In preferred embodiments, the step of providing a continuous flow reactor may further comprise a provision of a reactor which oscillatory system is configured to generate an oscillatory flow with a maximum flow ranging from 1 to 500 times the average flow rate of the first time characteristic. A respective oscillatory system allows an adjustment of the oscillatory flow to construction details of the at least one flow channel and to the viscosity and other characteristics of the reaction mixture processed inside the at least one flow channel.

In further advantageous embodiments, the inlet system is also in fluid communication with a preceding reactor and configured for transferring a combination of substances representing a preprocessed reaction mixture from the preceding reactor into the at least one flow channel, and/or the outlet system is also in fluid communication with a subsequent reactor and configured for transferring a reaction product present at the second end of the at least one flow channel to the subsequent reactor. The transfer of the substances is effected by the controller configured to control the inlet and the outlet system in the required way.

It is noted that the features of the reactor disclosed above in the context of the method for a continuous preparation of organic peroxides likewise qualify as features of the continuous flow reactor apparatus.

A method and apparatus as described above is favorably used for a preparation of organic peroxides in pure and/or diluted form selected from the following peroxide classes—diacyl peroxides, peroxyesters, peroxycarbonate esters, peroxydicarbonates, hydroperoxides, dialkyl peroxides, ketone peroxides, peroxyketals, monoperoxide ketals, peroxycarboxylic acids—and mixtures thereof:

diacyl peroxides, as for example decanoyl peroxide, lauroyl peroxide, benzoyl peroxide, o-methylbenzoyl peroxide, 3,5,5-trimethylhexanoyl peroxide;

peroxyesters, as for example 1,1-dimethyl-3-hydroxybutyl peroxyneodecanoate, α-cumyl peroxyneodecanoate, α-cumyl peroxyneoheptanoate, tert-amyl peroxyne-odecanoate, tert-butyl peroxyneodecanoate, tert-amyl peroxy-pivalate, tert-butyl per-oxypivalate, 2,5-dimethyl-2,5-di (2-ethyl hexanoylperoxy) hexane, tert-amyl peroxy-2-ethyl hexanoate, tert-butyl peroxy-2-ethyl hexanoate, tert-amyl peroxyacetate, tert-butyl peroxyacetate, tert-amyl perbenzoate, tert-butyl perbenzoate, tert-butylperoctoate;

peroxycarbonate esters, as for example OO-tert-amyl-O-(2-ethylhexyl) monoperoxy-carbonate, OO-tert-butyl-O-isopropyl monoperoxy-carbonate, OO-tert-butyl 1-(2-ethylhexyl) monoperoxy-carbonate, poly (tert-butyl peroxycarbonate) polyether;

peroxydicarbonates, as for example di (n-propyl) peroxydicarbonate, di (sec-butyl) peroxydi carbonate, di (2-ethylhexyl) peroxydicarbonate;

hydroperoxides, as for example cumene hydroperoxide, tert-amyl hydroperoxide, tert-butyl hydroperoxide;

dialkyl peroxides, as for example di-tert-amyl peroxide, di-tert-butyl peroxide, 2,5-dimethyl-2,5-di (tert-butylperoxy)-hexane, 2,5-dimethyl-2,5-di (tert-butyl-peroxy)-hex-ine;

ketone peroxides, as for example cyclohexanon peroxide, methyl ethyl ketone peroxide, methyl isobutyl ketone peroxide, acetyl acetone peroxide;

peroxyketals, as for example 1,1-di (tert-butylperoxy)-3,3,5-trimethylcyclohexane, 1,1-di (tert-butylperoxy) cyclohexane, 1,1-di (tert-amylperoxy) cyclohexane, n-butyl 4,4-di (tert-butylperoxy) valerate, ethyl 3,3-di (tert-amylperoxy) butyrate, ethyl 3,3-di (tert-butylperoxy) butyrate;

monoperoxyketals (ether peroxides), as for example 1-methoxy-1-(tert-amylperoxy) cyclohexane;

peroxycarboxylic acids, as for example succinic acid peroxide, perpropionic acid.

The inventions relates also to a continuous flow reactor comprising at least one flow channel configured as a reaction zone; an inlet system in fluid communication with a first end of the at least one flow channel and configured for introducing two or more substances or a combination of substances into the at least one flow channel; an outlet system in fluid communication with a second end of the at least one flow channel, the second end being located downstream of the first end and the outlet system being configured for extracting a reaction product present at the second end; an oscillatory system configured for superimposing an oscillatory flow on the flow of substances passing through the at least one flow channel, the oscillatory being effected in at least a section of the at least one flow channel; and a controller configured to control the inlet system to introduce, according to a first time characteristic, at least two substances or a combination of substances into the at least one flow channel, the oscillatory system to superimpose an oscillatory flow on at least a part of the flow of substances passing through the at least one flow channel, and the outlet system to extract, on an ongoing basis, the reaction product formed in the flow channel from the substances introduced such that the output mass flow rate corresponding to the sum of the input mass flow rates.

Further embodiments are detailed below:

it further comprises a temperature control system adapted to control the temperature profile along the length of the flow channel, and with the controller being further adapted for controlling the temperature control system to control the temperature profile along the at least one flow channel;

the oscillatory system comprises an oscillatory flow generating device mounted in fluid communication with the at least one flow channel at a first position and a hydraulic accumulator mounted in fluid communication with the at least one flow channel at a second position different from the first position;

the at least one flow channel comprises a first flow channel and a second flow channel, a first end of the first flow channel being in fluid communication with the inlet system and a second end of the first flow channel being in fluid communication with a first end of the second flow channel, the reactor further comprising a recirculation system configured for reintroducing a portion of the reaction mixture output from the second end of the first flow channel into the first flow channel upstream of its second end, and wherein the controller is further adapted to control the recirculation system to reintroduce a portion of the reaction mixture output from the second end of the first flow channel into the first flow channel upstream of its second end;

the first flow channel is formed by three flow channel modules connected in series, whereby the first flow channel module and the second flow channel module are each formed by split-and-recombine reactor, while the third flow channel module is formed by a meandering channel reactor, and wherein the inlet system is configured to introduce a first substance to a first inlet of the first flow channel module and to introduce a second substance to a first inlet of the second flow channel module, with the outlet of the first flow channel module being in fluid communication with a second inlet of the second flow channel module, the outlet of the second flow channel module being in fluid communication with the inlet of the third flow channel module, and the outlet of the third flow channel module being in fluid communication with a recirculation system configured for reintroducing a portion of the reaction mixture output from the third flow channel module into a second inlet of the first flow channel module;

the recirculation system comprises the oscillatory flow generating device and wherein the hydraulic accumulator is in fluid communication with the second end of the second flow channel;

the temperature control system comprises a first heat exchange system and a second heat exchange system, the first heat exchange system adapted for a heat exchange with the first flow channel and the second heat exchange system adapted for a heat exchange with the second flow channel, and wherein the controller is further adapted to control the temperature profile along the first flow channel separate from the temperature profile along the second flow channel;

it further comprises at least one additional inlet system configured for introducing one or more substances into the at least one flow channel downstream of its first end, with the controller being further configured to control the additional inlet system for introducing one or more additional substances into the at least one flow channel downstream of its first end according to a second time characteristic, and to control the outlet system to effect the output mass flow rate further also including the additional input mass rate;

the oscillatory system is configured to generate an oscillatory flow having a frequency of between 0.1 Hz and 500 Hz, preferably of between 1 to 50 Hz, and more preferably of between 2 Hz to 25 Hz;

the oscillatory system is configured to generate an oscillatory flow with a maximum flow from a range of 1 to 500 times the average flow rate of the first time characteristic.

The starting materials for the preparation of an organic peroxide using a process according to the present invention are known to a person skilled in the art.

The following reaction schemes illustrate the preparation of different peroxide classes and show the materials basically required (diluents and/or other possible/necessary additives are not shown; acid chlorides could as well be acid anhydrides):

Diacyl peroxides: Acid chlorides and hydrogen peroxide form diacyl peroxides.

$RC(O)Cl+H_2O_2+2NaOH/KOH \rightarrow RC(O)OOC(O)R+2H_2O+2NaCl/KCl$

Peroxyesters: Acid chlorides and organic hydroperoxides form peroxyesters.

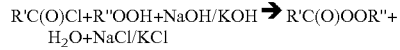
$R'C(O)Cl+R''OOH+NaOH/KOH \rightarrow R'C(O)OOR''+H_2O+NaCl/KCl$

Peroxycarbonate esters: Chloroformates and organic hydroperoxides form peroxycarbonats.

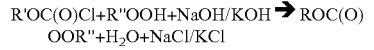
$R'OC(O)Cl+R''OOH+NaOH/KOH \rightarrow ROC(O)OOR''+H_2O+NaCl/KCl$

Peroxydicarbonates: Chloroformates and hydrogen peroxide form peroxydicarbonats.

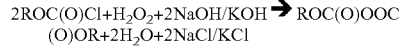
$2ROC(O)Cl+H_2O_2+2NaOH/KOH \rightarrow ROC(O)OOC(O)OR+2H_2O+2NaCl/KCl$ Hydroperoxides: Alcohols and hydrogen peroxide form hydroperoxides (for example with an acid like $H_2SO_4$ as catalyst).

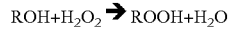
$ROH+H_2O_2 \rightarrow ROOH+H_2O$

Dialkyl peroxides: Alcohols and hydrogen peroxide form hydroperoxides (for example with an acid like $H_2SO_4$ as catalyst).

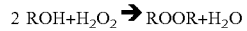
$2\ ROH+H_2O_2 \rightarrow ROOR+H_2O$

Ketone peroxides: Ketones and hydrogen peroxide form keton peroxides (for example with an acid like $H_2SO_4$ as catalyst).

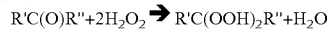
$R'C(O)R''+2H_2O_2 \rightarrow R'C(OOH)_2R''+H_2O$

Peroxyketals: Ketones and organic hydroperoxides form peroxyketals (for example with an acid like $H_2SO_4$ as catalyst).

$R'C(O)R''+2R'''OOH \rightarrow R'C(OOR''')_2R''+H_2O$

Monoperoxyketals (ether peroxides): Ketones, alcohols and organic hydroperoxides form monoperoxyketals (for example with an acid like $H_2SO_4$ as catalyst).

$R'C(O)R''+R'''OH+R''''OOH \rightarrow R'C(OR''')(OOR'''')R''+H_2O$

Peroxycarboxylic acids: Carbonic acid and hydrogen peroxide form peracids.

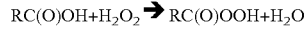
$RC(O)OH+H_2O_2 \rightarrow RC(O)OOH+H_2O$

Further features of the invention will be apparent from the following description of exemplary embodiments, the claims, and the attached figures. It is noted that embodiments of the present invention may implement the features described below in the context of particular embodiments in different combinations than provided by the exemplary embodiments. The present invention is therefore only limited by the scope of the attached claims and not by any of the exemplary embodiments below.

SHORT DESCRIPTION OF THE FIGURES

When explaining the present invention in more detail with respect to special embodiments, reference is made to the enclosed drawings, in which FIG. 1 is a schematic representation of a first configuration of an apparatus providing a continuous flow mixing reactor enabling a superposition of an oscillatory flow on a steady flow of a reaction mixture.

Figure 2:
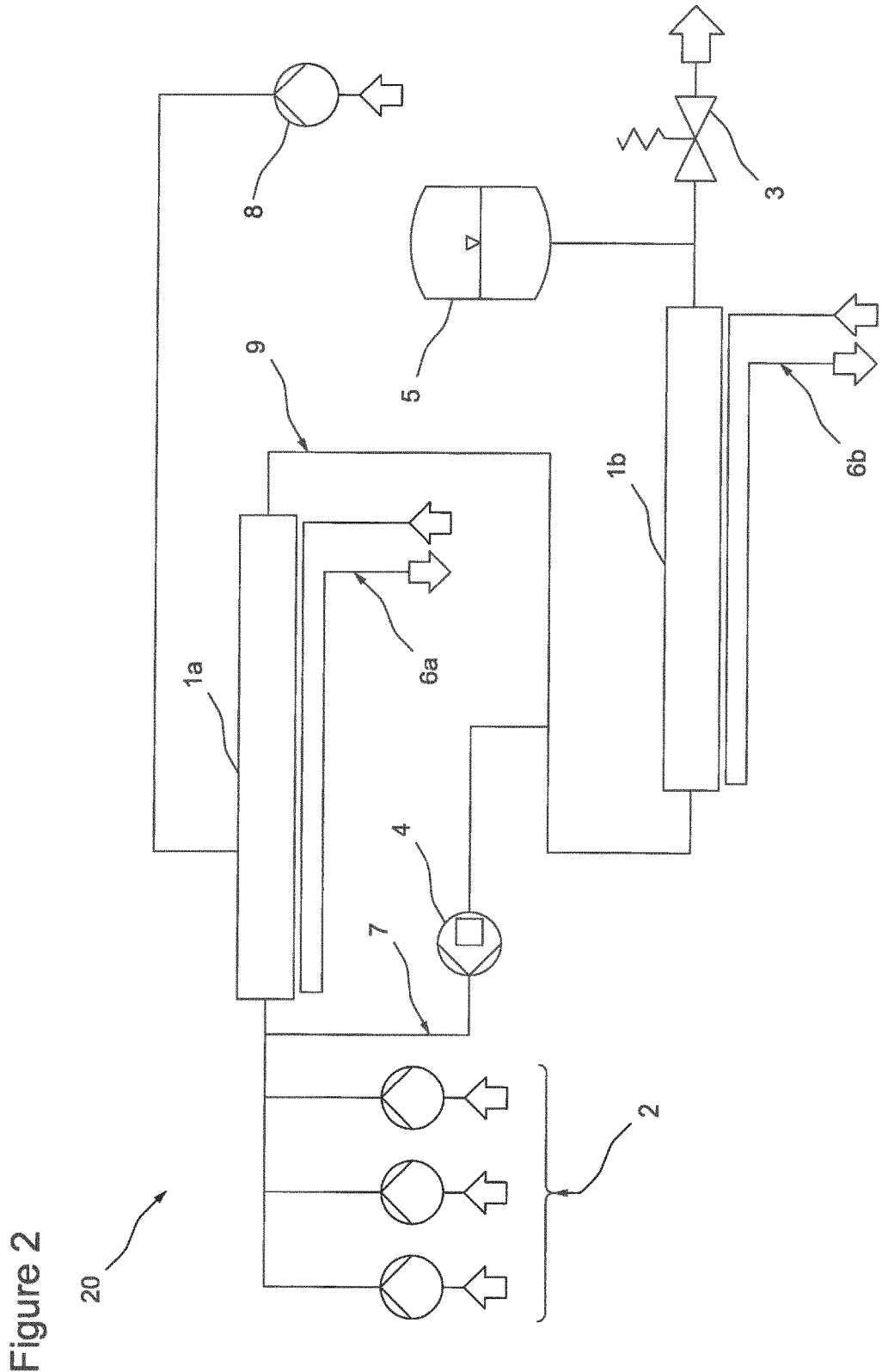
Figure 3:
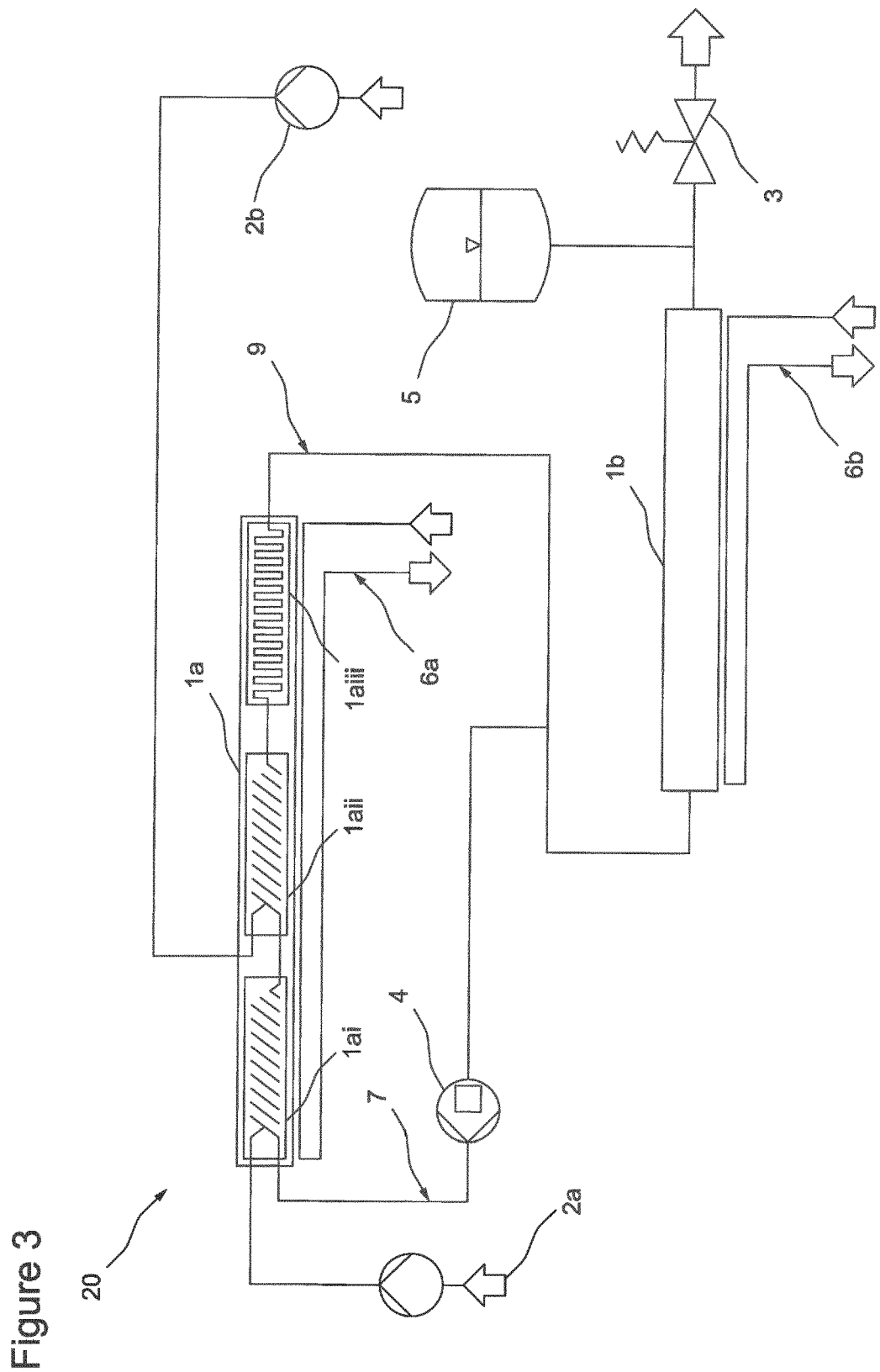
Figure 4:
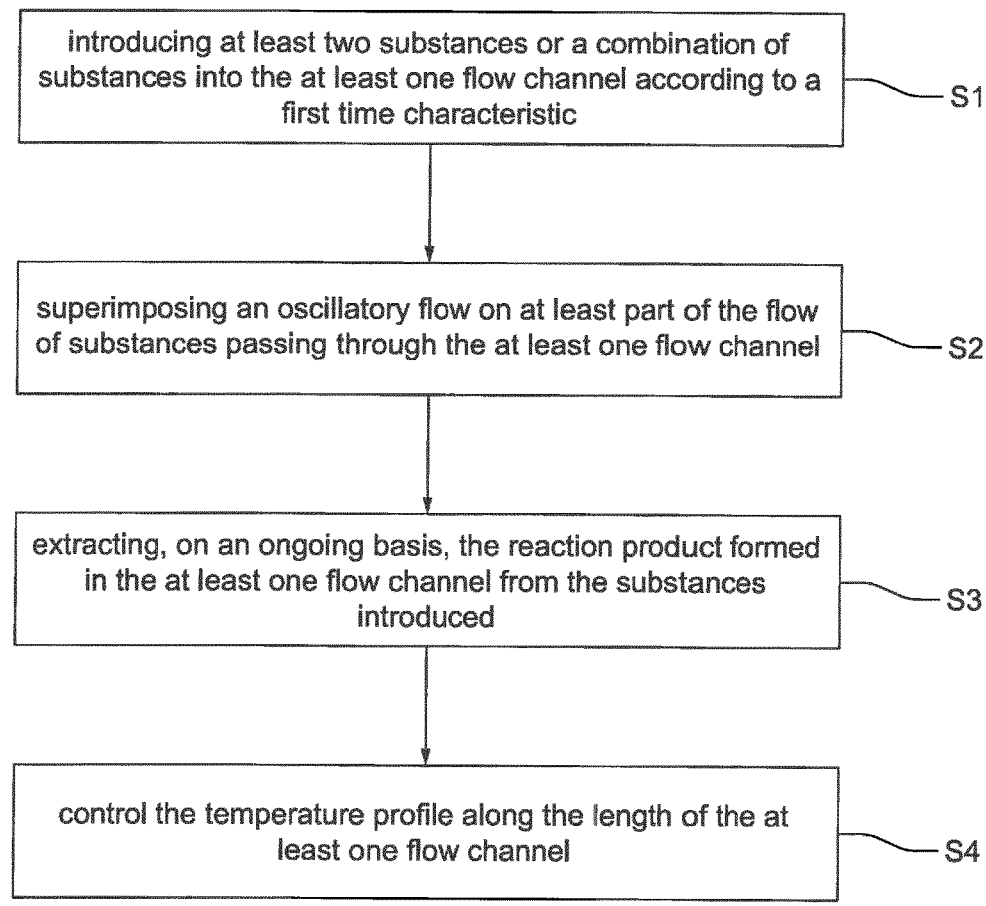

FIG. 2 is a schematic representation of a second configuration of an apparatus providing a continuous flow mixing reactor where a loop reaction zone is located upstream of another reaction zone configured for superimposing an oscillatory flow on a steady flow of a reaction mixture, FIG. 3 is a schematic representation of a third configuration of an apparatus where a loop reaction zone having three reactor modules is located upstream of another reaction zone configured for superimposing an oscillatory flow on a steady flow of a reaction mixture, and FIG. 4 is a flow chart illustrating the basic steps of a method for a continuous preparation of organic peroxides using an oscillatory flow superimposed on a steady flow of a reaction mixture.

DETAILED DESCRIPTION OF THE INVENTION

In the exemplary embodiments described below, components that are alike in function and structure are referenced as far as possible by alike reference numerals. Therefore, to under-stand the features of the individual components of a specific embodiment, the description of other embodiments and the summary of the disclosure should be referred to.

The schematic of FIG. 1 illustrates a first embodiment 10 of an apparatus representing a continuous flow reactor. The substances and or combination of substances forming the starting materials are introduced into a reaction zone 1 via an inlet system 2. The substance or substances resulting from a process taking place in the reaction zone 1 are output via an outlet system 3. Inlet system 2 and outlet system 3 are configured to generate a steady flow of substances between them. The inlet system 2 is usually adapted for actively introducing the starting materials into the reaction zone 1, while the outlet system 3 may in some embodiments be implemented as a passive device like the one illustrated in FIG. 1. Other embodiments have also the outlet system implemented as an active device, which extracts the reaction product actively on an ongoing basis.

As already mentioned above, the term "steady flow" is meant here to characterize a flow that does not change its general direction of flow and which time behavior is, except for initial and final phases of the preparation procedure, substantially unchanging in time, i.e. the flow rate is either virtually constant or follows a repetitive pattern, as in the case of pulsating flows like those resulting from using a displacement pump.

The continuous flow reactor 10 further comprises an oscillatory system configured for superimposing an oscillatory flow on the steady flow effected by the inlet system in either direct or indirect cooperation with the outlet system. Although any oscillatory system will be practica-ble that shifts the fluid inside the reactor zone 1 back and forth for a certain length, preferred embodiments of the oscillatory system comprise a displacement mechanism 4 in combination with an expansion tank 5, like a hydraulic accumulator or the like. The surges created by the displacement mechanism 4, e.g. a membrane pump, a piston pump or the like, are received by the expansion tank 5, e.g. a hydraulic accumulator or the like, and returned from the expansion tank in the suction cycle of the displacement mechanism.

The reaction zone comprises at least one flow channel 1 providing a fluid communication between its upstream first end and its downstream second end. The inlet system 2 is in fluid communication with the first end of the at least one flow channel. The outlet system 3 is in fluid communication with the second end of the at least one flow channel.

The at least one flow channel 1 may be formed by a tube, which length is basically defined by the product of the reaction time required for a given organic peroxide to be prepared and the average flow rate of the corresponding reaction mixture inside the tube. The inner diameter of the tube determines the capacity of the reactor. The inner diameter further depends on the characteristics of the oscillatory flow, that is to say, the inner diameter is chosen such that the oscillatory flow conditions generated by the oscillatory system enable turbulences inside the tube that provide the desired mixing of the reaction mixture components. In other words, the inner diameter of the tube and the characteristics of the oscillatory flow are designed for achieving a flow characterized by a Reynolds number of 3,000 or higher. For a thorough mixing of components, usually flows characterized by a Reynolds number of 4,000 and above are preferred.

To achieve a good mixing of components at comparatively lower flow rates, other types of flow channels may also be used like e.g. those described in the published International patent applications WO 2014/044624 A1 or WO 2012/095176 A1, where the creation of turbulences is improved by providing a flow pathway having several directional changes. A directional pathway change forces a fluid flow, in the present case of a reaction mixture for preparing an organic peroxide usually a liquid flow, to change direction. Respective directional changes or flow redirections introduce vortices resulting in turbulences mixing the reaction mixture components. The cross-sections of the pathways may be of various shapes provided that they may not give rise to a formation of dead zones where the local flow rate is to low to support the reaction. Preferred embodiments have flow channels with circular, annular, square or rectangular cross-sectional shapes. The cross-sectional shape may also vary along the flow-way. The flow channel or channels may also be provided by an assembly formed from plate structures as e.g. shown in WO 2007/125091 A1. The flow channel(s) may also be formed as recesses in a plate, whereby several plates may be sandwiched to form a reaction zone with the individual flow channel connected in parallel and/or in series. The plates may be heat exchange plates with channels allowing circulation of a heat transfer fluid formed therein or every other plate may be used for the heat exchange fluid while the re-maining plate(s) form the flow channel(s) for the actual reaction zone.

The cross-sectional dimensions of a flow channel affect the latters heat dissipation or heat exchange capacity. The ratio of the boundary surface of a flow channel to the volume enclosed by a flow channel's boundary surface decreases with increasing size of the flow channel's smaller cross-sectional dimension and results in a higher temperature difference between an innermost and an outermost location of the flow channel. The space-time-yield of a flow channel with a poor heat dissipation characteristic will therefore be low. For higher production volumes or productions on an industrial scale, several narrower flow channels may therefore be arranged in parallel. Since the pressure drop along a flow channel in-creases when the cross-sectional area of the flow channel decreases, flow channels should not be designed with cross sections too small; otherwise a pressure drop might result that will be too difficult to handle.

Cross-sectional flow channels can be characterized by their so-called hydraulic diameter, which is defined as four times the ratio of the flow channel's cross-sectional area to the wet-ted perimeter of the cross section. The hydraulic diameters range preferably from 0.5 mm to 100 mm, and more preferably from 2 to 50 mm. The ration between the flow channel surfaces and the flow channel's internal volume is preferably 20 $m^2/m^3$ or higher.

The temperature profile along the reaction zone is preferably controlled using a heat transfer fluid being in thermal contact with the reactor walls surrounding the at least one flow channels 1. The temperature profile can be adjusted to provide reaction temperatures below as well as above the SADT defined for an organic peroxide received in a usual size container, e.g. a container with 25 kg capacity. Reaction temperatures higher than an SADT are possible due to the efficient heat dissipation provided by the flow channel structures qualified for a continuous flow reactor explained above.

The temperature profile may advantageously be adjusted to local requirements of the reaction process by providing more than one heat transfer fluid loops 6 or circuits along the at least one flow channel 1. The heat transfer fluid loops 6 form part of a temperature control system (not further shown in the Figures) allowing to set the desired temperature profile inside the at least one flow channel. The heat transfer fluid(s) can be used for cooling as well as heating the reaction mixture, i.e. for transferring into or out from the reaction mixture.

In the embodiment illustrated in FIG. 1, the oscillatory systems effects an oscillatory flow along the entire length of the at least one flow channel 1. Other embodiments have the oscillatory flow be effected along a section of the flow channel 1 only, preferably a downstream section. A respective configuration can be used to prevent a formation of so called "hot spots" in the upstream part of the at least one flow channel where the concentration of reactants is the highest and a fine dispersion of the phases would result in a too fast reaction. When using a system based on a displacement mechanism 4 cooperating with an expansion tank or expansion chamber 5, the volume displaced is preferably chosen such that the associated movement of the flow of substances in the reaction zone corresponds to only a part of the length of the at least one flow channel. The oscillatory system preferably effects an oscillatory flow having a frequency of 0.1 Hz or higher but not exceeding 500 Hz, more preferably of 1 Hz or more but not higher than 50 Hz, and even more preferably of 2 Hz and higher, but not exceeding 25 Hz. Frequency and displacement volume further preferably adjusted to achieve an oscillatory flow which maximum flow rate equals or corresponds to a multiple of the average flow rate of the steady flow effected by the introduction (and possibly extraction) of substances into the at least one flow channel. In preferred embodiments, the multiple can be up to about five hundred times the average flow rate of the steady flow.

The inlet system 2 preferably has more than on inlet for introducing the starting materials in a well dosed manner. The input system may be formed by displacements pumps or other types of dosing systems. Instead of several independent pumps, a multihead pump may be used, where all pump mechanisms are operated simultaneously by one drive, e.g. an elec-tronically controlled motor. The starting materials that may be introduced using the inlet system 2 depend on the produced peroxide classes as shown above. It is noted that the number of inlets depends on the respective process performed in the reactor and may therefor differ from three inlets as illustrated in FIGS. 1 and 2.

To enable an addition of reactants, additives or diluents further downstream into the at least one flow channel or even downstream of the reactor zone, the apparatus 10 or 20 (see FIG. 2) may further comprise an additional inlet system 8 (shown in FIG. 2 only) for adding a respective substance or mixture of substances at the desired position to the flow of substances. It is appreciated that although the additional inlet system 8 is illustrated to have one inlet only, it may also have more than one inlet which may combine to introduce a mixture at a certain point of the flow channel and/or not combine to add substances or mixtures of substances at different points of the at least one flow channel. The latter may for instance be used to distribute the addition of a certain reactant along the pathway of the reaction zone.

The outlet system 3 may be formed by a backflow prevention device like a double check valve or other type of pressure retention device, or any other suited device, for instance a pump, if need be in combination with a pulsation damper.

Apparatus 10 and 20 each further comprise a controller (not shown in the Figures) for controlling its sub-systems, i.e. the inlet system for introducing the starting materials in the desired manner, the oscillatory system to produce turbulences to the desired extent, the temperature control system to adjust the reaction temperatures along the at least one flow channel to the desired temperature profile, and, if applicable, the outlet system to extract the reaction product at a rate that corresponds to the sum of input rates of the starting materials and as may be the case also those of the additionally introduced substances. In other words, the outlet extracts the reaction product with a rate corresponding to the input rate of the substances.

FIG. 2 illustrates a second embodiment 20 of an apparatus representing a continuous flow reactor. Different to the first embodiment 10, the at least one flow channel 1 is composed of two separate flow channels 1a and 1b connected in series. The line 9 connecting the first flow channel 1a with the downstream second flow channel 1b is tapped to form a fluid communication between the downstream and the upstream ends of the first flow channel 1a. This connection 7 serves a recirculation of part of the reaction mixture output from the downstream end of the first flow channel 1a. In one configuration, the recirculation is effected by a pump disposed in the recirculation line 7, while the displacement mechanism 4 of the oscillatory system is connected to the upstream end of the second flow channel 1b or further downstream of this end.

Another configuration, which is shown in FIG. 2 and characterized by a reduced capital expenditure, effects the recirculation by the displacement mechanism 4 of the oscillatory system disposed in the recirculation line 7. The expansion tank 5 of the oscillatory system is, like in embodiments according to FIG. 1, disposed between the downstream end of the second flow channel and the outlet system 3, or fluidly connected to the second flow channel 1b somewhere between its upstream and downstream ends. In the suction cycle, the displacement mechanism 4 draws in material from the line connecting the downstream end of the first flow channel 1a with the upstream end of the second flow channel 1b. In the discharge cycle, the displacement mechanism 4 discharges the material into the first flow channel 1b through its upstream end. This results in both, a recirculation of part of the material flowing through the first flow channel 1a and an oscillatory flow superimposed on the flow of substances passing the second flow channel 1b.

Implementing the at least one flow channel 1 in form of two serially connected separate flow channels 1a and 1b, and driving the first flow channel in recirculation forms two consecutive reaction sub-zones serving different purposes. In the first reaction sub-zone, where the concentration of the reactants is the highest, part of the reaction mixture flows in a loop enabling, since only the discharge cycle of the displacement mechanism is used to keep up the recirculation, a good macro mixing of the reactants resulting in a uniform distribution of the reactants in the reaction mixture but with droplet sizes big enough to avoid undesired hot spots and to ensure lower reaction kinetics and thus less generation of heat. Due to the recirculation, the average flow rate inside the first flow channel 1a is higher than the flow rate induced by the inlet system 2 distributing the heat generated in the course of the reaction more evenly along the length of the first reaction sub-zone thus enabling a better temperature control at this early stage of the reaction. Since the reaction conditions in the first reaction sub-zone differ from that in the downstream second reaction sub-zone, the first flow channel is, as shown in FIG. 2, preferably equipped with a separate heat exchange system 6a that can be operated independent of the other heat exchange system 6b provided for the second reaction sub-zone 1b.

Different to the first flow channel 1a, both cycles of the displacement mechanism 4 act on the second flow channel 1b. Due to the cooperation with the hydraulic accumulator 5, the displacement mechanism 4 effects a back and forth shifting of the reaction mixture in the second flow channel 1b giving rise a micro mixing resulting in finely dispersed droplets of small sizes and boosting the reaction kinetics. According to the different reaction kinetics, the temperature profile in the second flow channel is preferably controlled by a separate heat exchange system 6b, configured for an operation independent of the heat exchange system 6a.

Like in the embodiments according to FIG. 1, also embodiments according to FIG. 2 comprise a controller (not shown) for controlling the individual components of the apparatus 20 to perform a method for preparing an organic peroxide from a class as described above.

FIG. 3 shows a modification of the apparatus illustrated in FIG. 2. In this embodiment, the flow channel 1a comprises three flow channel modules 1ai, 1aii, and 1aiii, whereby the first two flow channel modules 1ai and 1aii are each formed by a split-and-recombine reactor having its reaction channels arranged in a herringbone structure similar to that disclosed in WO 2014/044624 A1. A reactor having a meandering channel structure similar to that disclosed in FIG. 6 of WO 2012/095176 A1 forms the third flow channel module 1aiii. The inlet system consists of two inlets, a first inlet 2a for introducing a first starting material into the first flow channel module 1ai, where it is mixed with the part recirculated from the output of the third flow channel module 1aiii, and a second inlet 2b introducing a second starting material into the second flow channel module 1aii, where it is mixed with the output from the first flow channel module 1ai. The configuration further improves the temperature control at an early stage of the reaction. It is appreciated that also embodiments according to FIG. 3 comprise a controller (not shown) for controlling the individual components of the apparatus 20 to perform a method for preparing an organic peroxide from a class as described above. The first starting material may for instance be an aqueous solution of tert-butyl potassium hydroperoxide (TBKP), while the second starting material may be 2-ethylhexanoyl chloride (EHC).

The apparatuses illustrated in FIGS. 1 to 3 may be stand-alone reactors or each form a sub-reactor of a more complex, multistage reactor design. When forming part of a multistage reactor, the inlet system 2 is usually part of a preceding reactor located upstream of the at least one flow channel 1, and/or the outlet system 3 is usually part of a succeeding reactor located downstream of the at least one flow channel 1. In configurations like these, only part of the total reaction is performed in the at least one flow channel.

The basic steps of a method for preparing an organic peroxide are illustrated in the flow chart of FIG. 4. The arrows connecting the individual steps of the procedure are not meant to indicate any chronological order. The arrow rather illustrate the direction of the mass flow or flow of substances in the procedure. Once the process is established, all process steps are performed simultaneously. Step S1, i.e. introducing at least two substances or a combination of substances into the at least one flow channel according to a first time characteristic, is performed by the controller of the apparatus 10 or 20 acting on the inlet system. Step S2, i.e. superimposing an oscillatory flow on at least part of the flow of substances passing through the at least one flow channel, is performed by the controller of the apparatus 10 or 20 acting on the oscillatory system. Step S3, i.e. extracting, on an ongoing basis, the reaction product formed in the at least one flow channel from the substances introduced, is performed by the controller of the apparatus 10 or 20 acting on the outlet system. Most reactions require step S4 which is likewise performed by the controller of the apparatus 10 or 20, this time acting on the temperature control system to control the temperature profile along the length of the at least one flow channel, whereby the different sections of the flow channel or different sub-reaction zones may be controlled independent from each other.

The potential of the present invention is illustrated by the below example using an apparatus with two reaction sub-zones according to the types of embodiments characterized by FIG. 3. The apparatus used was a glass-type reactor with a hydraulic diameter of 1 mm. The total volume of the first reaction zone is about 1.5 ml and is the sum of the volumes of the first flow channel modules 1ai (0.2 ml), the second flow channel module 1aii (again 0.2 ml), and the third flow channel modules 1aiii (1.1 ml), that of the second reaction zone 1.1 ml; recirculation and oscillation flow where both effected by one plunger pump disposed in the recirculation loop as indicated in FIG. 3 below. The pump was operated at a speed 1,000 rpm and thus the oscillation flow frequency was about 17 Hz. The ratio of the maximum oscillatory flow rate to the steady flow rate was about 14.

Starting materials used were an aqueous solution of tert-butyl potassium hydroperoxide (TBKP) and 2-ethylhexanoyl chloride (EHC). The TBKP was introduced with a syringe pump at a steady flow of 7.93 mmol/min on the upper end of the first reactor sub-zone. The EHC were introduced with a syringe pump at a steady flow of 6.15 mmol/min between the two split-and-recombine reactors of the first reaction sub-zone. For temperature control the reactor system was inserted in a bath. The reaction temperature was set to 47° C. and the over-all residence time was about 1 minute. The reaction product tert-butyl peroxy-2-ethylhexanoate (TBPEH) was separated after being output from the second reaction sub-zone with a steady flow of 5.86 mmol/min. This represents a yield of more than 95% based on TBKP and is comparable to the yields achieved in DD 128663 (about 90%) and WO 2008/006666 A1 (98.5%). With a total reaction volume of 3.7 ml (2*0.2 ml+2*1.1 ml+1.1 ml for piping) the calculated space-time-yield is 20 kg/l·h. This is eight times the space-time-yield achieved with a reactor according to WO 2008/006666 A1 (2.5 kg/l·h) and about five times the space-time-yield achieved with a reactor according to DD 128663 (3.6 kg/l·h). The conversion of the EHC is 100% and the selectivity for TBPEH better than 95%. Compared to the results disclosed by Fritzsche and Knorr in the publications cited above, better selectivity, conversion and yield are achieved.

While the above description explains the present disclosure with reference to certain exemplary embodiments, it is evident that many alternatives, modifications, and variations will be apparent to those skilled in the art. Accordingly, the exemplary embodiments of the disclosure set forth herein serve the purpose to illustrate the disclosure and are not intended to limit it in any way. Various changes may be made to the embodiments described without departing from the spirit and scope of the present disclosure as defined in the following claims.

The invention claimed is:

1. A method for a continuous preparation of organic peroxides comprising:
   providing a continuous flow reactor having:
      at least one flow channel configured as a reaction zone;
      an inlet system in fluid communication with a first end of the at least one flow channel and configured for introducing two or more substances or a combination of substances into the at least one flow channel;
      an outlet system in fluid communication with a second end of the at least one flow channel, the second end being located downstream of the first end and the outlet system being configured for extracting reaction products present at the second end; and
      an oscillatory system configured for superimposing an oscillatory flow on the flow of substances passing through the at least one flow channel, the oscillatory being effected in at least a section of the at least one flow channel;
   (S1) introducing, according to a first time characteristic, at least two substances or a combination of substances into the at least one flow channel using the inlet system,
   (S2) superimposing by use of the oscillatory system an oscillatory flow on at least a part of the flow of substances passing through the at least one flow channel to create turbulences in the flow of substances, wherein the substances are reacted in the one flow channel to produce the organic peroxides,
   (S3) extracting, on an ongoing basis and by using the outlet system, the reaction products formed in the at least one flow channel from the substances introduced, the output mass flow rate corresponding to the sum of the input mass flow rates.

2. The method according to claim 1, wherein providing a continuous flow reactor comprises providing a reactor further having a temperature control system adapted to control the temperature profile along the length of the at least one flow channel, and wherein the method further comprises a step (S4) of controlling the temperature profile along the at least one flow channel using the temperature control system.

3. The method according to claim 1, wherein introducing the at least two substances according to the first time characteristic comprises an introduction of at least one of the two substances in a constant or in a pulsating manner.

4. The method according to claim 1, wherein superimposing an oscillatory flow on at least a part of the flow of substances passing through the at least one flow channel comprises a use of an oscillatory system having an oscillatory flow generating device being in fluid communication with the at least one flow channel at a first position and a hydraulic accumulator being in fluid communication with the at least one flow channel at a second position different from the first position.

5. The method according to claim 4, wherein providing a continuous flow reactor comprises providing a reactor wherein at least one flow channel comprises a first flow channel and a second flow channel, a first end of the first flow channel being in fluid communication with the inlet system and a second end of the first flow channel being in fluid communication with a first end of the second flow channel, the reactor further comprising a recirculation system configured for reintroducing a portion of the reaction mixture output from the second end of the first flow channel into the first flow channel upstream of its second end, and wherein the method further comprises a step for reintroducing a portion of the reaction mixture output from the second end of the first flow channel into the first flow channel upstream of its second end using the recirculation system.

6. The method according to claim 5, wherein providing a continuous flow reactor comprises providing the first flow channel formed by three flow channel modules connected in series, whereby the first flow channel module and the second flow channel module are each formed by split-and-recombine reactor, while the third flow channel module is formed by a meandering channel reactor, and wherein the inlet system is configured to introduce a first substance to a first inlet of the first flow channel module and to introduce a second substance to a first inlet of the second flow channel module, with the outlet of the first flow channel module being in fluid communication with a second inlet of the second flow channel module, the outlet of the second flow channel module being in fluid communication with the inlet of the third flow channel module, and the outlet of the third flow channel module being in fluid communication with a recirculation system configured for reintroducing a portion of the reaction mixture output from the third flow channel module into a second inlet of the first flow channel module.

7. The method according to claim 5, wherein the recirculation system comprises the oscillatory flow generating device and wherein the hydraulic accumulator is in fluid communication with the second end of the second flow channel.

8. The method according to claim 5, wherein controlling the temperature profile along the at least one flow channel using the temperature control system comprises a use of a temperature control system having a first heat exchange system and a second heat exchange system, the first heat exchange system adapted for a heat exchange with the first flow channel and the second heat exchange system adapted for a heat exchange with the second flow channel, for controlling the temperature profile along the first flow channel separate from the temperature profile along the second flow channel.

9. The method according to claim 1, wherein providing a continuous flow reactor comprises providing a reactor further having an additional inlet system configured for introducing one or more substances into the at least one flow channel downstream of its first end.

10. The method according to claim 1, wherein providing a continuous flow reactor comprises providing a reactor wherein the oscillatory system is configured to generate an oscillatory flow having a frequency of between 0.1 Hz and 500 Hz.

11. The method according to claim 1, wherein providing a continuous flow reactor comprises providing a reactor wherein the oscillatory system is configured to generate an oscillatory flow with a maximum flow from a range of 1 to 500 times the average flow rate of the first time characteristic.

12. The method according to claim 1, wherein the inlet system is further in fluid communication with a preceding reactor and configured for transferring a combination of substances representing a preprocessed reaction mixture from the preceding reactor into the at least one flow channel, and/or wherein the outlet system is further in fluid communication with a subsequent reactor and configured for transferring a reaction product present at the second end to the subsequent reactor.

13. The method according to claim 1, wherein the organic peroxides prepared are selected from the group consisting of one of the following peroxide classes: diacyl peroxides, peroxyesters, peroxycarbonate esters, peroxydicarbonates, hydroperoxides, dialkyl peroxides, ketone peroxides, peroxyketals, monoperoxyketals, peroxycarboxylic acids, and mixtures thereof.

* * * * *